United States Patent [19]

Forder

[11] 4,344,420
[45] Aug. 17, 1982

[54] SURGICAL RETRACTOR

[76] Inventor: William C. F. Forder, 33 Rosehill Ave., Apt. 1903, Toronto, Ontario, Canada, M4T 1G4

[21] Appl. No.: 150,083

[22] Filed: May 15, 1980

[30] Foreign Application Priority Data

May 2, 1980 [CA] Canada .................................. 351176

[51] Int. Cl.³ ......................... A61B 17/02; A61B 1/32
[52] U.S. Cl. .................................................... 128/20
[58] Field of Search ......................................... 128/20

[56] References Cited

U.S. PATENT DOCUMENTS

| | | | |
|---|---|---|---|
| 20,905 | 7/1858 | Thomas | 128/20 |
| 475,975 | 5/1892 | Clough | 128/20 |
| 497,064 | 5/1893 | Van Meter | 128/20 |
| 2,450,194 | 9/1948 | Glaser | 128/20 |
| 2,693,795 | 11/1954 | Grieshaber | 128/20 |
| 3,965,890 | 6/1976 | Gauthier | 128/20 |
| 4,254,763 | 3/1981 | McCready et al. | 128/20 |

*Primary Examiner*—Kyle L. Howell
*Assistant Examiner*—Nancy A. B. Swisher

[57] ABSTRACT

This invention relates to an improved surgical retractor. The retractor has a cross member, a fixed arm, a sliding arm, and an improved spring locking means for securely locating the sliding arm on the cross member. The arms each have inwardly directed blade members which extend into the wound to hold it open. The present structure allows the surgeon to directly and accurately feel the force of the arms on the wound during insertion and the locking mechanism enables him to quickly, easily and safely lock the arms in a selected position. In one embodiment used for kidney surgery, the arms are contoured to the patient's body to allow the cross member to be located against the patient's flank. This provides the surgeon with increased access over the cross member and avoids the danger that he will lean on the cross member, causing the retractor to twist in the wound or ever to flip right out of the wound.

13 Claims, 6 Drawing Figures

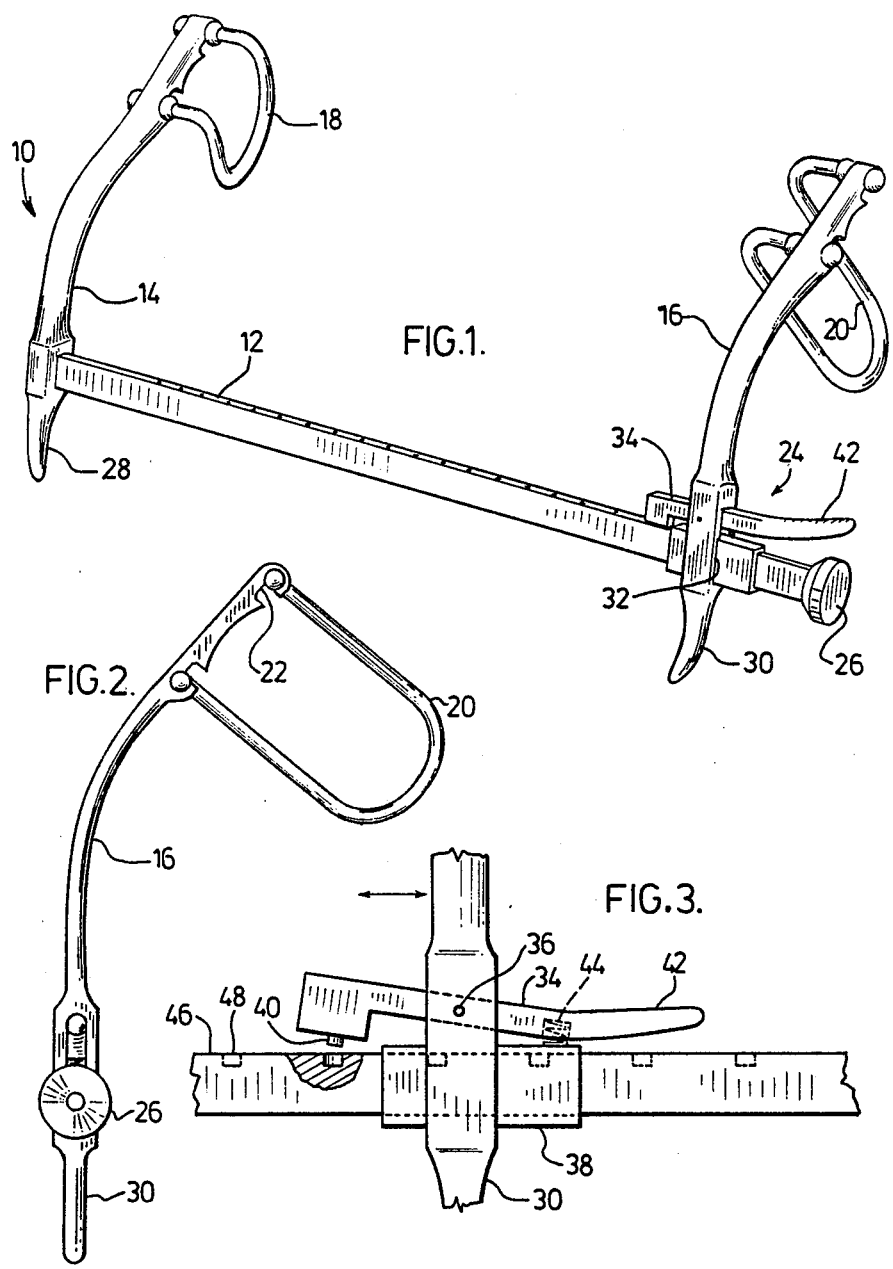

SURGICAL RETRACTOR

BACKGROUND OF THE INVENTION

This invention relates to surgical instruments and more particularly to an improved surgical retractor.

Surgical regractors are well known and have been in widespread use for many years. While they are very useful and necessary in maintaining the body open during various types of major surgery, the present retractors have the disadvantage that, on occasion, their use may result in inadvertant damage to the internal organs of the patient by moving during the procedure and/or to accidental and dangerous disruption of the surgical procedure by collapsing and falling out of the wound if the patient "bucks" under general anaesthesia. Simple respirations can also cause disruption of the position of the instrument especially in the flank. This sudden closure of the wound often occurs at a critical time during the operative procedure which may have severe consequences.

As shown in U.S. Pat. Nos. 1,311,313 which issued July 29, 1919 to Brix and 2,850,008 which issued Sept. 2, 1958 to Resch, some of the known retractors do not have any positive locking means and rely only on the sliding arm being slightly askew to maintain it in the desired position. This is a very dangerous situation because during surgery the retractor is under a very considerable load and the patient is constantly moving (i.e. respirations) and if the retractor is accidentally jarred or levered, it could immediately release causing irreparable damage during a crucial or delicate part of the operation. U.S. Pat. Nos. 1,706,500 which issued Mar. 26, 1929 to Smith and 1,963,173 which issued June 19, 1934 to Morin show attempts to overcome this problem using ratchet means and while this is an improvement it still is not satisfactory. Another attempt to overcome this problem is to provide a retractor with a screw lock, but this similarly is not sufficiently positive, is awkward to use and may come free during the procedure and get lost in the peritoneal cavity of retroperitoneal space. Another attempted solution which has not been entirely satisfactory is shown in U.S. Pat. No. 3,227,156 which issued Jan. 4, 1966 to Gauthier.

As shown in U.S. Pat. No. 2,450,194 which issued Sept. 28, 1948 to Glaser ratchet retractors may also have the disadvantage that too much force may be applied to the body opening resulting in permanent damage to the surrounding area. Mechanically assisting the forcible opening of the body opening has even been known to result in the breaking of ribs and damaging of organs. It is normally desirable to spread the wound open as far as the incision will permit without causing any damage. Therefore, it is essential that the surgeon be able to accurately feel the force being applied by the retractor arms during extension and also be able to quickly and conveniently positively secure the locking means when the desired position is reached.

Another important source of potential retractor damage to the body arises if the retractor cross member is not positioned against the patient's abdomen or flank during use. While this problem does not normally occur during abdominal surgery, it presently is an accepted problem during kidney surgery. In standard renal surgical procedures, the surgeon stands at the patient's back and leans over and in fact touches the retractor cross member as the arms extend rearwardly from the incision. If the surgeon's body accidentally exerts any downward force on the retractor cross member, it has the effect of pivoting the blades of the retractor upwards in the wound resulting in possible damage to major blood vessels or internal viscera such as the spleen, liver, lungs, etc. Occasionally this results in the retractor pivoting sufficiently to be twisted right out of the wound causing it to close suddenly. To make things worse, this normally happens during a critical part of the operation when the surgeon is concentrating on what he is doing and may lean over a little further than normal or may lean from fatigue.

SUMMARY OF THE INVENTION

Accordingly, it is an object of the invention to at least partially overcome these disadvantages by providing an improved surgical retractor having improved spring locking means.

To this end, in one of its aspects, the invention provides a surgical retractor comprising a pair of arms mounted on an elongated cross member, one of the arms being fixed to the cross member adjacent one end of the cross member, the other of the arms being slidably mounted on the cross member. Each of the arms have blade means extending therefrom adjacent their free ends whereby opposite edges of a surgical incision may be engaged by the blade means and separated by sliding said other arm along the cross member away from the fixed arm. A plurality of aligning holes are spaced along the cross member, and locking means are included whereby the said arm may be securely retained in a selected one of a plurality of positions along the cross member. The locking means comprises a detent member pivotally mounted on said other arm, the detent member has a trigger portion and a projecting pin portion adapted to be engagingly received in one of said holes, the detent member is spring loaded to bias the pin portion against the cross member. Said other arm may thereby be secured in a selected locked position by holding the trigger portion of the detent member, sliding said other arm along the cross member, and releasing the trigger portion to result in the pin portion becoming engaged in the first of said holes it reaches after release. Thus the said other arm will be securely retained in said locked position against the pressure of the incision against the arms until the trigger portion is released.

In another of its aspects, the invention provides this surgical retractor wherein the arms are curved in the direction in which the blade means extend into the incision to the extent that when used in renal surgery, the retractor will be contoured in a position against the patient's flank.

Further objects and advantages of the invention will appear from the following description taken together with the accompanying drawings.

BRIEF DESCRIPTION OF THE DRAWINGS

FIG. 1 is a perspective view of a surgical retractor according to a preferred embodiment of the invention;

FIG. 2 is an end elevation view of the retractor seen in FIG. 1;

FIG. 3 shows the locking mechanism of the retractor seen in FIG. 1;

DETAILED DESCRIPTION OF THE DRAWINGS

Figure 4:
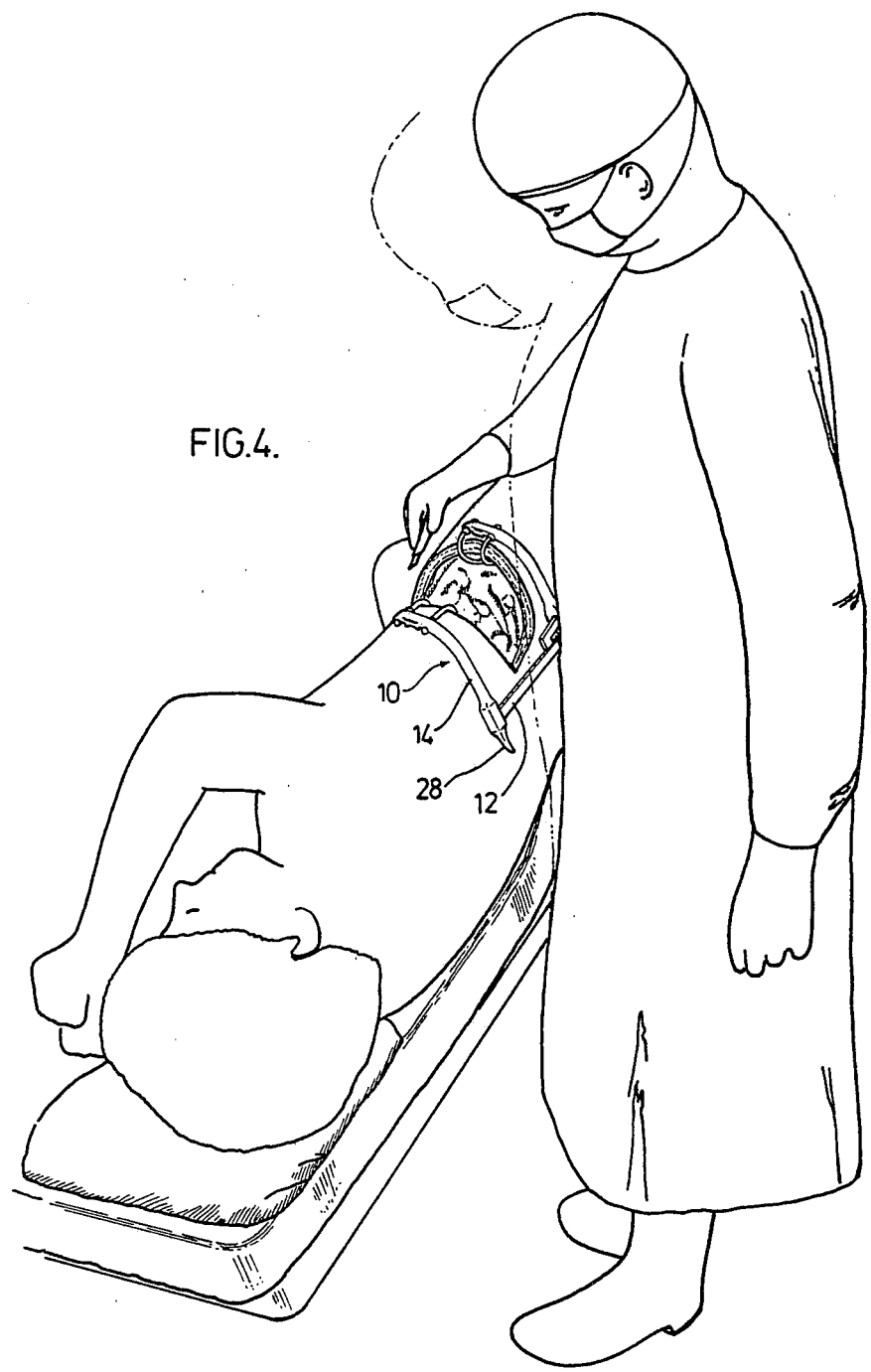
FIG. 4 shows a typical position of the patient, retractor, and surgeon during renal surgery.

Reference is first made to FIGS. 1 to 3 which show a retractor 10 having a cross member 12 and a pair of arms 14, 16. The arms 14, 16 each have a U-shaped wire spring blade member 18, 20 which face towards each other and are removably engaged in slots 22. As may be seen, one of the arms 14 is fixed to the cross member 12 at one end, while the other arm 16 slides along the cross member 12 until it is locked in a selected position by locking mechanism 24. A stop 26 is provided at the other end of the cross member 12 to avoid any danger of arm 16 sliding right off. The blade members 18, 20 are bent in the same direction to be inserted into the wound and, as clearly seen in FIG. 2, the arms 14, 16 are both curved in this same direction lateral to the cross member 12. Both of the arms 14, 16 also have slightly curved thumb holds 28, 30 which project downwardly from the cross member 12.

The sliding arm 16 has an aperture 32 therethrough and the locking mechanism 24, which is clearly shown in FIG. 3, includes a detent member 34 which is pivotally mounted in the aperture 32 by pin 36. The sliding arm 16 is cast with a hollow sleeve portion 38 which extends beneath the detent member 34 and is shaped to slidably fit over the cross member 12. The detent member 34 having a projecting pin portion 40 at one end and a trigger portion 42 at the other. A spring 44 is seated in the detent member 34 and abuts on the sleeve 38 to bias the pin portion 40 against a flat surface 46 of the cross member 12. A row of holes 48 is located on the flat surface 46, in alignment with the projecting pin portion 40 of the detent member 34. The projecting pin portion 40 is shaped to be securely seated under the force of the spring 44 in the first of the holes 48 it comes to as the arm 14 is slid along the cross member 12. In this embodiment, all components of the retractor 10 are made of stainless steel which has the combination of high strength and corrosion resistance necessary for surgical instruments. The stainless steel has a mat finish to reduce reflection from the surgical lights.

In use, the surgeon makes an incision in the desired location in the patient's body and inserts the blade members 18, 20 of the retractor 10 into it with the arms 14, 16 fairly close together. The blade members 18, 20 are interchangeable and will be made in different lengths and care must be taken that blades of the proper length are selected and the instrument is positioned in the wound so that they will not damage any body tissue or organs.

The surgeon is holding the retractor 10 with the cross member 12 towards him and the arms 14, 16 pointing away from him to the wound. His left hand holds the fixed arm 14 and his right hand holds the sliding arm 16 and they are gradually pulled apart to open the wound to the necessary extent. The hands are normally positioned with each thumb (first digit) on the respective thumb hold below the cross member 12 and the fingers above the cross member with the arms 14, 16 extending between the index and middle fingers of the respective hands. In this position, the third and forth digits of the right hand automatically rest on the trigger portion 42 of the detent member 34, which is depressed during opening.

When the necessary sized wound opening is reached, the trigger portion 42 is released and the pin portion 40 of the detent member 34 will snap into the appropriate hole 48, securely locking the retractor 10 in that position. Even if the retractor 10 slips or is accidentally released, the force of the spring 44 will automatically engage the pin portion 40 in the first hole in the closing direction. During wound opening, the resistance of the body opening must be carefully felt in the surgeon's hands to avoid too much tension being applied. If too much force is required before the necessary opening is obtained, the incision must be enlarged to avoid damaging viscera, blood vessels and ribs and the retractor may be quickly and conveniently locked in any intermediate position to facilitate this. If adjustment in opening size is required during the operation, this may be easily carried out without danger of the retractor slipping or releasing. When the operative procedure is completed, this sequence is reversed and the wire blade members 18, 20 are withdrawn from the incision.

This particular embodiment is particularly adapted for renal surgery with the patient, incision, retractor and surgeon oriented in the normal positions shown in FIG. 4. As may be seen, the curved arms 14, 16 are contoured to the patient's flank allowing the cross member 12 to lie adjacent the patient's flank in the inserted position. This provides two distinct advantages. Firstly, the retractor cross bar 12 is down out of the way which provides the surgeon with improved access to the wound and relieves his concern that he will inadvertently lean on the retractor and pivot the blades in the wound or, even wores, flip the retractor right out of the wound. Secondly, even if he does lean against the retractor, it cannot pivot because it is already up against the patient's body. Furthermore, in this position, there is minimal risk of the locking mechanism 24 accidentally releasing because the trigger portion 40 is adjacent the cross member 12 and in the plane of the arms at that point.

Figure 5:
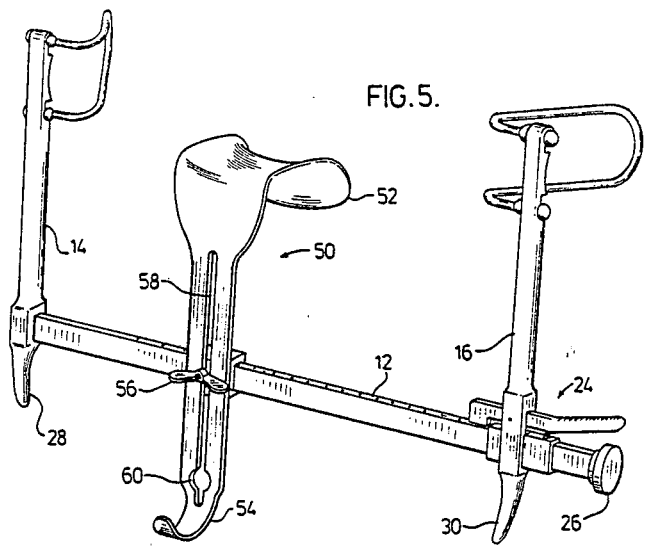
FIG. 5 is a perspective view of a retractor according to another embodiment of the invention.

FIG. 5 illustrates the structure of a second embodiment of the retractor, and as many features are identical to those of the first embodiment, features common to both embodiments are described and illustrated using the same reference numerals. In this embodiment, the cross member 12, the locking mechanism 24, and the blade members 18, 20 are identical to those of the first embodiment, but the arms 14, 16 are straight rather than curved, and a mid-visceral blade 50 extends from the cross member 12. The mid-visceral blade 50 also slides on the cross member 12 and has a curved scoop portion 52 and a curved finger portion 54 at opposite end. A wing nut 56 extends through a slot 58 with an enlarged portion 60 which provides for removal of the mid-visceral blade 50 from the retractor.

This embodiment is for use as an anterior abdominal retractor for general surgery, gynecology, renal transplants in the groin area and also for lower portions of the ureter. The method of use is essentially the same as that described above in regard to the first embodiment except that, following insertion, the mid-visceral blade may be drawn back and locked by wing nut 56 to retain the intestines out of the surgeon's way during the operation. It will be appreciated that the location of the incision in the abdomen normally allows the cross member 12 to be located in a secure position against the patient's body without the contoured arms being required.

Figure 6:
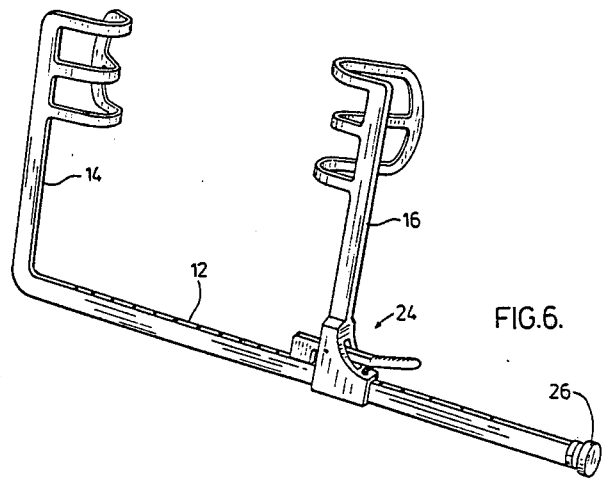
FIG. 6 is a perspective view of a retractor according to a further embodiment of the invention.

FIG. 6 illustrates the structure of a third embodiment of the invention which is a larger adbominal retractor for use in major surgery such as a retroperitoneal lymphadenectomy or radical cancer surgery such as a cystectomy and ileo-conduit procedure for bladder cancer. Once again, the same reference numerals are used as in the first embodiment. In this embodiment, the blades 18, 20 are cast integrally with the arms 14, 16 and are of a stronger construction. The locking mechansim 24 is similarly cast in a slightly different configuration, but is essentially the same. As may be seen, the arms 14, 16 are straight as the incision is normally in the abdomen where the retractor may be inserted so that it is in a secure position against the patient's body.

The use of this instrument is essentially the same as that described above, although the size and duration of these operations make it even more critical, if possible, that the retractor be securely and safely positioned in the wound. As mentioned above, particularly during long operations, the patient may occasionally "buck" violently under the effect of the anesthetic with disasterous results if the retractor is not secure. Vision in the wound is another frequently critical aspect which may be improved by increasing the stability of the retractor in the wound and improving the surgeon's access to it.

Although the disclosure describes and illustrates several preferred embodiments of the retractor, it is not to be construed in a limiting sense. Many variations and modifications may now occur to those skilled in the art. For instance, it will be apparent that the fixed and sliding arms may be reversed to provide a retractor with locking mechanism to be operated by the left hand.

The embodiments of the invention in which an exclusive property or privilege is claimed are defined as follows:

1. A surgical retractor for renal surgery consisting essentially of a pair of arm means mounted on a single, generally rectangular in cross section, elongated cross member, a first arm means of the pair being generally fixed to the cross member adjacent one end thereof, the second arm means of the pair being generally fixed to a rectangular sleeve member slidably mounted on said cross member, each of the arm means having blade means extending therefrom adjacent their free ends away from said cross member for engaging the opposite edges of a surgical wound and separating such edges by sliding the second arm means along the cross member away from the first arm means, a plurality of aligned holes being spaced along said cross member, and pin-nosed pawl locking means for securely retaining the second arm means in a selected one of a plurality of positions along the cross member in spaced relationship to a selected one of said plurality of aligned holes, said pin-nosed pawl locking means comprising a pawl pivotably mounted on the second arm means, said pawl member having a projecting pin portion adapted to be engagingly received in one of said holes and a digitably engageable trigger portion for releasing said pin portion from engaging reception in said one of said holes, said pawl member being spring loaded to bias the pin portion against said cross member, a first side of said rectangular cross bar lying against the patient during surgical use, a second side of said rectangular cross bar having said arm means extending therefrom at generally right angles to said first side, said plurality of aligned holes and said pin-nosed pawl locking means being located on said second side, said first and second arm means being curved in a direction which is generally toward said first side of said cross member, and in the direction in which the blade means extend into the surgical wound, so that the renal retractor lies generally adjacent to and in contact with the patient's flank during use in renal surgery, a third side of said rectangular cross member being located generally opposite said first side of said cross member being substantially free of projections extending beyond said sleeve member so as to permit greater accessibility to the wound and reduce accidental contact by operating room personnel with said renal retractor during use, said second arm means, said cross member, said sleeve member, and said locking means cooperating to provide a smooth, very sensitive, and non-obstructing translation of said second arm means along said cross bar, combined with a positive self-locking yet easily released locking mechanism for easy positioning and retention of the instrument in said surgical wound in that said second arm may be secured in the selected locked position along the cross member by holding the trigger portion of said pawl locking means to disengage the projecting pin portion from said holes and sliding said second arm means, said sleeve member, and pin-nosed pawl locking means along said cross member to a desired position, whereupon digital release of said trigger portion causes the pin portion to become engaged in the first of the holes the pin portion reaches after such release to securely retain said second arm means in the thus locked position against pressure of the incision against the arm means until the trigger portion is digitally engaged.

2. Surgical retractor as claimed in claim 1, wherein the said rectangular sleeve is of a length such as to engage the rectangular cross member to a degree as to reduce rotational torque applied to the rectangular cross member by said sleeve so as to provide high flexural and torsional strength of the retractor while reducing binding or gripping of the second arm means.

3. Surgical retractor as claimed in claim 1, wherein said retractor additionally includes a thumb-engageable lever extending from said sleeve in a direction generally opposite from said second arm means.

4. Surgical retractor of claim 1, wherein said pin-nosed pawl locking means securely retain said second arm means against pressure exerted on said second arm means in either direction along the cross member.

5. A surgical retractor consisting essentially of a pair of arm means mounted on a single, generally rectangular in cross section, elongated cross member, a first arm means of the pair being generally fixed to the cross member adjacent one end thereof, the second arm means of the pair being generally fixed to a rectangular sleeve member slidably mounted on said cross member, each of the arm means extending from the same side of the cross member and having blade means extending therefrom adjacent their free ends away from said cross member for engaging the opposite edges of a surgical wound and separating such edges by sliding the second arm means along the cross member away from the first arm means, a plurality of aligned holes being spaced along said cross member along said same side, and pin-nosed pawl locking means for securely retaining the second arm means against forces exerted in either direction along the cross member in a selected one of a plurality of positions along the cross member in spaced relationship to a selected one of said plurality of aligned holes, said pin-nosed pawl locking means comprising a pawl member pivotably mounted on the second arm means and extending therefrom on both sides along the cross member, said pawl member having a projecting pin portion adapted to be engagingly received in one of said holes and a digitally engageable trigger portion for releasing said pin portion from engaging reception in said one of said holes, said pawl member being spring loaded to bias the pin portion against said cross member, said second arm means, said cross member, said sleeve member, and said locking means cooperating to provide a smooth, very sensitive, and non-obstructing translation of said second arm means along said cross bar, combined with a positive self-locking yet easily released locking mechanism for easy positioning and retention of the instrument in said surgical wound in that said second arm may be secured in the selected locked position along the cross member by holding the trigger portion of said pawl locking means to disengage the projecting pin portion from said holes and sliding said second arm means, said sleeve member, and pin-nosed pawl locking means along said cross member to a desired position, whereupon digital release of said trigger portion causes the pin portion to become engaged in the first of the holes the pin portion reaches after such release to securely retain said second arm means in the thus locked position against pressure of the incision against the arm means or against other pressures in either direction along the cross member until the trigger portion is digitally engaged.

6. Surgical retractor as claimed in claim 5, wherein each of the arm means have a pair of slots adjacent their free ends away from said cross member, each slot of the pair generally facing the other slot of the pair, said blade means resiliently engaging said slots to maintain said blade means under compression between said slots to securely retain said blade means on said arm means during use, but permit rapid change of the blade means when desired.

7. Surgical retractor of claim 5, wherein said retractor additionally includes a mid-visceral blade arm extending from said cross member between said first arm means and said second arm means, and in the same general direction as said arm means.

8. Surgical retractor as claimed in claim 5, wherein the said rectangular sleeve is of an axial length such as to engage the rectangular cross member to a degree as to reduce rotational torque applied to the rectangular cross member by said sleeve so as to provide high flexural and torsional strength of the retractor while reducing binding or gripping of the second arm means.

9. Surgical retractor as claimed in claim 8, wherein said retractor additionally includes a thumb-engageable lever extending from said sleeve in a direction generally opposite from said second arm means.

10. A surgical retractor as claimed in claim 5, wherein said first and second arm means are curved in a direction which is generally toward said first side of said cross member, and in the direction in which the blade means extend into the surgical wound, so that the surgical retractor lies generally adjacent to and in contact with the patient's flank during use in renal surgery.

11. A surgical retractor as claimed in claim 10, wherein the third side of said rectangular cross member, lying generally opposite said first side of said cross member, is substantially free of projections extending beyond said sleeve member so as to permit greater accessibility to the wound and reduce accidental contact by operating room personnel with said surgical retractor during use.

12. A surgical retractor consisting essentially of a pair of arm means mounted on a single, generally rectangular in cross section, elongated cross member, a first arm means of the pair being generally fixed to the cross member adjacent one end thereof, the second arm means of the pair being generally fixed to a rectangular sleeve member slidably mounted on said cross member, each of the arm means having blade means extending therefrom adjacent their free ends away from said cross member for engaging the opposite edges of a surgical wound and separating such edges by sliding the second arm means along the cross member away from the first arm means, a pair of slots on each of the arm means adjacent their free ends away from said cross member, each slot of the pair generally facing the other slot of the pair, said blade means resiliently engaging said slots to maintain said blade means under compression between said slots to securely retain said blade means on said arm means during use but permit rapid change of the blade means when desired, a plurality of aligned holes being spaced along said cross member, and pin-nosed pawl locking means for securely retaining the second arm means in a selected one of a plurality of positions along the cross member in spaced relationship to a selected one of said plurality of aligned holes, said pin-nosed pawl locking means comprising a pawl member pivotably mounted on the second arm means, said pawl member having a projecting pin portion adapted to be engagingly received in one of said holes and a digitally engageable trigger portion for releasing said pin portion for engaging reception in said one of said holes, said pawl member being spring loaded to bias the pin portion against said cross member, said second arm means, said cross member, said sleeve member, and said locking means cooperating to provide a smooth, very sensitive, and nonobstructing translation of said second arm means along said cross bar, combined with a positive self-locking yet easily released locking mechanism for easy positioning and retention of the instrument in said surgical wound in that said second arm may be secured in the selected locked position along the cross member by holding the trigger portion of said pawl locking means to disengage the projecting pin portion from said holes and sliding said second arm means, said sleeve member, and pin-nosed pawl locking means along said cross member to a desired position, whereupon digital release of said trigger portion causes the pin portion to become engaged in the first of the holes the pin portion reaches after such release to securely retain said second arm means in the thus locked position against pressure of the incision against the arm means until the trigger portion is digitally engaged.

13. A surgical retractor for renal surgery consisting essentially of a pair of arm means mounted on a single, generally rectangular in cross section, elongated cross member, a first arm means of the pair being generally fixed to the cross member adjacent one end thereof, the second arm means of the pair being generally fixed to a rectangular sleeve member slidably mounted on said cross member, each of the arm means having blade means extending therefrom adjacent their free ends away from said cross member for engaging the opposite edges of a surgical wound and separating such edges by sliding the second arm means along the cross member away from the first arm means, a pair of slots on each of the arm means adjacent their free ends away from said cross member, each slot of the pair generally facing the other slot of the pair, said blade means resiliently engaging said slots to maintain said blade means under compression between said slots to securely retain said blade means on said arm means during use but permit rapid change of the blade means when desired, a plurality of aligned holes being spaced along said cross member, and pin-nosed pawl locking means for securely retaining the second arm means in a selected one of a plurality of positions along the cross member in spaced relationship to a selected one of said plurality of aligned holes, said pin-nosed pawl locking means comprising a pawl pivotably mounted on the second arm means, said pawl member having a projecting pin portion adapted to be engagingly received in one of said holes and a digitally engageable trigger portion for releasing said pin portion for engaging reception in said one of said holes, said pawl member being spring loaded to bias the pin portion against said cross member, a first side of said rectangular cross bar lying against the patient during surgical use, a second side of said rectangular cross bar having said arm means extending therefrom at generally right angles to said first side, said plurality of aligned holes and said pin-nosed pawl locking means being located on said second side, said first and second arm means being curved in a direction which is generally towards said first side of said cross member, and in the direction in which the blade means extend into the surgical wound, so that the renal retractor lies generally adjacent to and in contact with the patient's flank during use in renal surgery, a third side of said rectangular cross member being located generally opposite said first side of said cross member being substantially free of projections extending beyond said sleeve member so as to permit greater accessibility to the wound and reduce accidental contact by operating room personnel with said retractor during use, said second arm means, said cross member, said sleeve member, and said locking means cooperating to provide a smooth, very sensitive, and non-obstructing translation of said second arm means along said cross bar, combined with a positive self-locking yet easily released locking mechanism for easy positioning and retention of the instrument in said surgical wound in that said second arm may be secured in the selected locked position along the cross member by holding the trigger portion of said pawl locking means to disengage the projecting pin portion from said holes and sliding said second arm means, said sleeve member, and pin-nosed pawl locking means along said cross member to a desired position, whereupon digital release of said trigger portion causes the pin portion to become engaged in the first of the holes the pin portion reaches after such release to securely retain said second arm means in the thus locked position against pressure of the incision against the arm means until the trigger portion is digitally engaged.

* * * * *